United States Patent [19]

Benabid

[11] Patent Number: 5,707,396
[45] Date of Patent: Jan. 13, 1998

[54] METHOD OF ARRESTING DEGENERATION OF THE SUBSTANTIA NIGRA BY HIGH FREQUENCY STIMULATION OF SUBTHALAMIC NUCLEUS

[75] Inventor: Alim Benabid, Grenoble, France

[73] Assignee: Institute National de la Sante de la Recherche Medicale (INSERM), Paris, France

[21] Appl. No.: 637,438

[22] Filed: Apr. 25, 1996

[51] Int. Cl.$^6$ .................................................. A61N 1/00
[52] U.S. Cl. ................................................ 607/2; 128/898
[58] Field of Search ............................ 607/72, 45, 117, 607/118, 2; 128/642, 898, 899

[56] References Cited

U.S. PATENT DOCUMENTS

| | | | |
|---|---|---|---|
| 3,850,161 | 11/1974 | Liss | 607/45 |
| 5,443,710 | 8/1995 | Broderick | 128/642 |
| 5,474,547 | 12/1995 | Aebischer et al. | 128/898 |

OTHER PUBLICATIONS

Mark Hallett, "The Plastic Brain," *Annals of Neurology*, vol. 38, No. 1, Jul. 1995.

C.W. Olanow et al., "The Effect of Deprenyl and Levodopa on the Progression of Parkinson's Disease," *Ann. Neurol.* 1995;38:771–777.

Stanley J. Appel, "A Unifying Hypothesis for the Cause of Amyotrophic Lateral Sclerosis, and Alzheimer Disease," *Ann. Neurol.* 1981;10:499–505.

J.T. Greenamyre, "Glutamate–dopamine Interactions in the Basal Ganglia: Relationship to Parkinson's Disease," *J. Neural Transm.* [GenSect] 1993;91:255–269.

Limousin et al "Effect on parkinsonian signs and symptoms of bilateral subthalamic nucleus stimulation" The Lancet vol. 345 Jan. 14, 1995.

Benabid et al "Long–term suppression of tremor by Chronic stimulation of the ventral intermediate thalamic nucleus" The Lancet, vol. 337, Feb. 16, 1991.

Benabid et al "Vim & STN Stimulation in Parkinson' disease" Abstracts of the Intl Congress of Movement Disorders 1994.

*Primary Examiner*—William E. Kamm
*Assistant Examiner*—George R. Evanisko
*Attorney, Agent, or Firm*—Banner & Witcoff, Ltd.

[57] ABSTRACT

A method of preventing further degeneration of the substantia nigra observed in patients with Parkinson's disease. High frequency electrical pulses are supplied to the subthalamic nucleus thereby blocking stimulation of the subthalamic nucleus

2 Claims, 1 Drawing Sheet

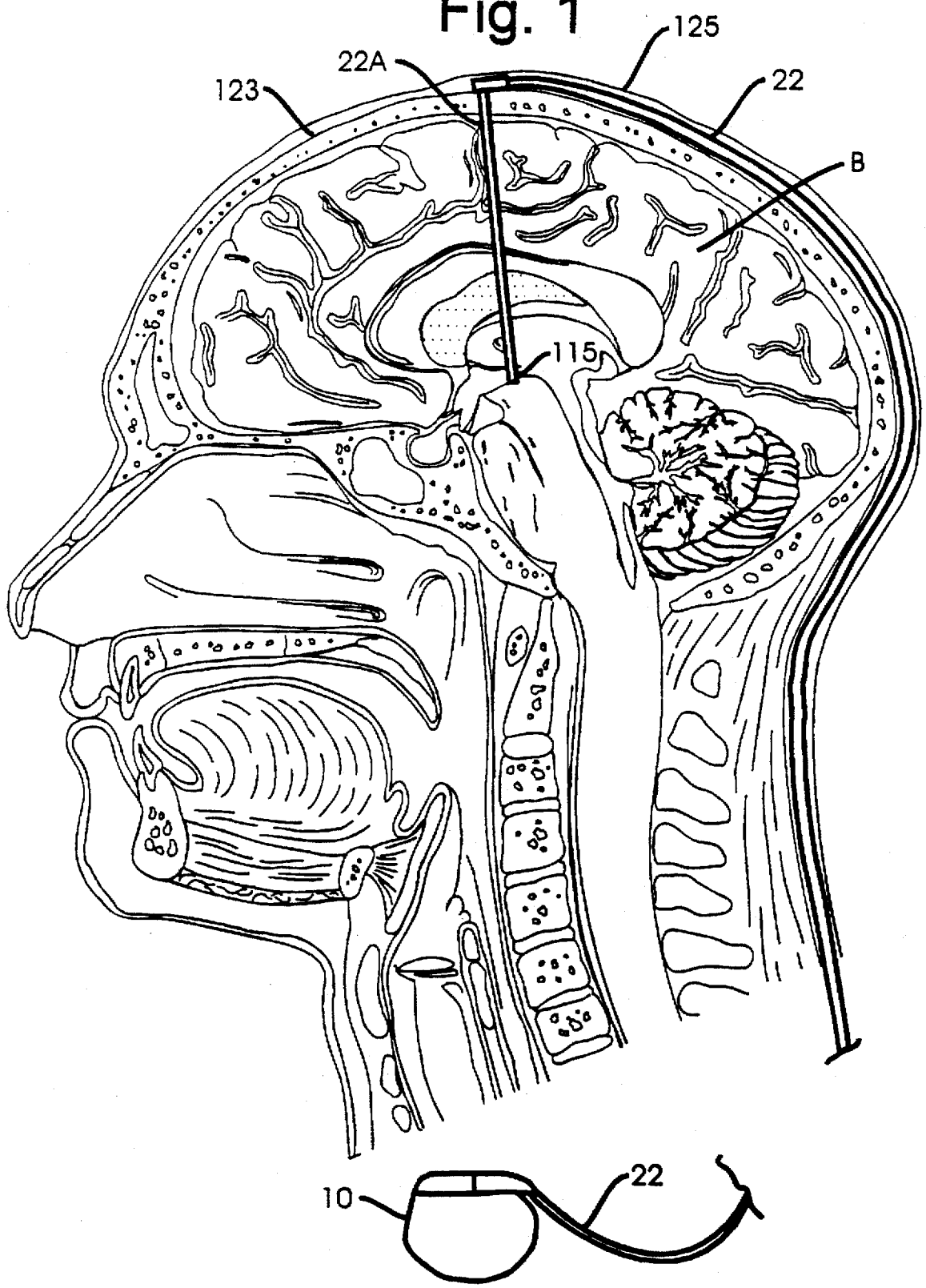

METHOD OF ARRESTING DEGENERATION OF THE SUBSTANTIA NIGRA BY HIGH FREQUENCY STIMULATION OF SUBTHALAMIC NUCLEUS

BACKGROUND OF THE INVENTION

1. Field of the Invention

This invention relates to brain stimulation techniques, and more particularly relates to such techniques for arresting degeneration of the substantia nigra by high frequency stimulation of the subthalamic nucleus.

2. Description of Related Art

Neuroscientists have recognized and continue to explore excitotoxicity, a phenomenon referring to excessive excitation of nerve cells leading to degeneration of the nervous system. This phenomena has been used to explain cell loss after stroke or some other hypoxic event. The research has focused on nerve cells that have glutamate neuro transmitter receptors especially susceptible to the sustained insult. Hyper excitation of these nerve cells is fundamental to the mechanism. (Rothman, S. M., Olney, J. W. (1987) *Trends Neurosci.* 10, 299–302). Researchers have also used excitotoxicity to explain the observed cell loss in the CA1 region of the Horn of Ammon in the dentate gyrus of hippocampus in patients and animal subjects that have suffered from seizure activity. Seizures can be viewed as a form of abnormal over excitation of the nerve cells in this region.

Typically, neuroscientists have focused on nerve cells that use the transmitter substance glutamate to communicate with target nerve cells; however, other excitatory amino acids (EAA) are included. When nerve cells are abnormally active, experiencing a lot of action potentials, they are believed to release excessive amounts of glutamate or other EAA at their synaptic terminals. The presence of excessive amounts of glutamate leads to toxic effects on the secondary nerve cells targeted by the hyperactive ones. These toxic effects are believed to be mediated by an accumulation of calcium.

Benabid et al. (*The Lancet*, Vol. 337:Feb. 16, 1991, pp 403–406) have shown that stimulation of the Vim nucleus of the Thalamus will block tremor. In this instance, stimulation at frequencies around 100 to 185 pulses per second accomplishes the same physiological response as a lesion of this region. Thus, it appears that stimulation inhibits the output of these cells to help reduce the tremor. Benabid's research team has extended this work to stimulation of the subthalamus in order to help reduce symptoms of motion disorders ("Vim and STN Stimulation in Parkinson's disease", *Movement Disorders*, Vol. 9, Supplement 1 (1994); "Effect on Parkinsonian signs and symptoms of bilateral subthalamic nucleus stimulation", *The Lancet*, Vol 345, Jan. 14, 1995.

Parkinson's disease is the result of degeneration of the substantia nigra pars compacta. The cells of subthalamus have been shown to use glutamate as the neurotransmitter effecting communication with their target cells of the basal ganglia. The state of hyperexcitation that exists in Parkinson's disease will cause an excessive release of glutamate. This, in theory, will lead to further degeneration via the mechanism described above.

SUMMARY OF THE INVENTION

The invention can treat Parkinson's disease by a method utilizing an implantable signal generator and an implantable electrode having a proximal end coupled to the signal generator and having a stimulation portion for stimulating the subthalamic nucleus of a brain. The electrode is implanted in the brain so that the stimulation portion lies in the subthalamic nucleus. The signal generator pulses the electrode at a rate high enough to block activity of the subthalamic nucleus to inhibit excessive release of glutamate at the terminal ends of the axons projecting from the subthalamic nucleus to the substantia nigra.

By using the foregoing method as soon as the onset of Parkinson's disease is diagnosed, further degeneration of the substantia nigra observed in patients with Parkinson's disease can be prevented.

BRIEF DESCRIPTION OF THE DRAWINGS

These and other advantages and features of the invention will become apparent upon reading the following detailed description and referring to the accompanying drawing in which like numbers refer to like parts throughout and in which:

FIG. 1 is a diagrammatic illustration of a stimulation electrode implanted in a brain according to a preferred embodiment of the present invention and a signal generator coupled to the electrode.

DESCRIPTION OF THE PREFERRED EMBODIMENTS

Referring to FIG. 1, a system or device 10 made in accordance with the preferred embodiment may be implanted below the skin of a patient. A lead 22A is positioned to stimulate the subthalamic nucleus in a brain (B). Device 10 may take the form of a signal generator Model 7424 manufactured by Medtronic, Inc. under the trademark Itrel II which is incorporated by reference. Lead 22A may take the form of any of the leads sold with the Model 7424 for deep brain stimulation. Lead 22A is coupled to device 10 by a conventional cable 22.

The distal end of lead 22A terminates in four stimulation electrodes generally designated 115 implanted into the subthalamic nucleus of the brain by conventional stereotactic surgical techniques. The implantation preferably is made as soon as Parkinson's disease is diagnosed. Each of the four electrodes is individually connected to device 10 through lead 22A and cable 22. Lead 22A is surgically implanted through a hole in the skull 123, and cable 22 is implanted between the skull and the scalp 125 as shown in FIG. 1. Cable 22 is joined to implanted device 10 in the manner shown.

Device 10 is programmed to produce pulses having a repetition rate of about 10–2500 Hz. At the stated frequency, stimulation of the subthalamic nucleus is blocked to inhibit excessive release of glutamate at the terminal ends of the axons projecting from the subthalamic nucleus to the substantia nigra. This method may prevent further degeneration of the substantia nigra observed in patients with Parkinson's disease.

By using the foregoing techniques, the effects of neurodegenerative disorders can be controlled with a degree of accuracy previously unattainable.

Those skilled in the art will recognize that the preferred embodiment may be altered or amended without departing from the true spirit and scope of the invention, as defined in the accompanying claims.

I claim:

1. A method of preventing further degeneration of a substantia nigra of a brain of a patient with Parkinson's disease by means of a signal generator and an implantable electrode having a proximal end and a stimulation portion utilized in conjunction with a subthalmic nucleus of said brain, said method comprising the steps of:

surgically implanting said electrode in the brain so that the stimulation portion lies in the subthalmic nucleus of the brain;

coupling said proximal end of said electrode to said signal generator; and operating said signal generator at a predetermined repetition rate high enough to block activity of the subthalmic nucleus to inhibit excessive release of glutamate at the terminal ends of the axons projecting from the subthalamic nucleus to the substantia nigra.

2. A method, as claimed in claim 1, wherein said repetition rate is about 10–2500 Hz.

* * * * *